US00PP20896P2

(12) United States Plant Patent
Hanes

(10) Patent No.: US PP20,896 P2
(45) Date of Patent: Mar. 30, 2010

(54) ***PELARGONIUM* PLANT NAMED 'AMRI PUR'**

(50) Latin Name: *Pelargonium×hortorum*
Varietal Denomination: Amri Pur

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/288,822

(22) Filed: Oct. 23, 2008

(51) Int. Cl.
*A01H 5/00* (2006.01)

(52) U.S. Cl. ..... Plt./329

(58) Field of Classification Search ..... Plt./329, Plt./325

See application file for complete search history.

*Primary Examiner*—June Hwu
(74) *Attorney, Agent, or Firm*—S. Matthew Edwards

(57) ABSTRACT

A new *Pelargonium* plant named 'Amri Pur,' particularly distinguished by the brilliant red-purple semi-double flowers, medium sized, round inflorescences well above the foliage, medium green foliage with strong zonation, and well-branched, rounded, medium to tall plant habit.

1 Drawing Sheet

Latin name of the genus and species of the plant claimed: *Pelargonium×hortorum.* varietal denomination: 'Amri Pur'.

BACKGROUND OF THE NEW PLANT

The present invention comprises a new zonal *Geranium,* botanically known as *Pelargonium×hortorum* and hereinafter referred to by the variety name 'Amri Pur.'

'Amri Pur' is a product of a planned breeding program. The new cultivar 'Amri Pur' has deep red-purple flowers with weak scarlet eyes, medium green foliage with strong zonation, and medium to tall, rounded plant habit.

'Amri Pur' originated from a hybridization made in the October 2004 in a controlled breeding program in Gilroy, Calif., U.S.A. The female parent was the unpatented seedling designated '10153-1,' with rose-red flower color. '10153-1' has more petals per flower and less tight plant habit than 'Amri Pur.'

The male parent of 'Amri Pur' was an unpatented hybrid seeding identified as '9843-2' with orchid flower color. '9843-2' has a less vigorous growth habit than 'Amri Pur.'

The resulting seeds were sown in March 2005. 'Amri Pur' was selected as one flowering plant within the progeny of the stated cross in May 2005 in a controlled environment in Gilroy, Calif.

The first act of asexual reproduction of 'Amri Pur' was accomplished when vegetative cuttings were propagated from the initial selection in the summer of 2005 in a controlled environment in Gilroy, Calif.

Horticultural examination of plants grown from cuttings of the plant initiated in the early spring of 2006 in Gilroy, Calif., and continuing thereafter, has demonstrated that the combination of characteristics as herein disclosed for 'Amri Pur' are firmly fixed and are retained through successive generations of asexual reproduction.

'Amri Pur' has not been observed under all possible environmental conditions. The phenotype may vary significantly with variations in environment such as temperature, light intensity and day length.

Plant Breeders' Rights for this cultivar was applied for in Canada on Dec. 24, 2007 and in Germany on Jun. 30, 2008.

'Amri Pur' has not been made publicly available more than one year prior to the filing of this application.

DESCRIPTION OF THE DRAWINGS

The accompanying photographic drawing shows typical flower and foliage characteristics of 'Amri Pur' with colors being as true as possible with an illustration of this type.

The photographic drawing shows a flowering potted plant of the new variety in a 6 inch pot and a close-up of the flowers.

Both of the photographs were taken in November 2007 in Gilroy, Calif. Both were grown in Gilroy, Calif. and were approximately two months old.

DETAILED BOTANICAL DESCRIPTION

The measurements were taken in Hillscheid, Germany, on Aug. 28, 2008 on about 6 month old plants that were growing outdoors in the trial field. Culture of these plants had started in early March when rooted young plants were planted into 12 cm pots and were grown out, unpinched, on benches in a greenhouse. In mid May they were transplanted, 3 each, into 42 cm tubs which were placed outdoors.

Color chart used: The Royal Horticultural Society Colour Chart (R.H.S.), 2001.

BRIEF SUMMARY OF INVENTION

The following observations, measurements, and comparisons describe plants grown indoors and outside in Hillscheid, Germany, and in Chatellerault, France. The following traits have been repeatedly observed and are determined to be basic characteristics of the new variety. The combination of these characteristics distinguishes this *Pelargonium* (common name zonal *Geranium*) as a new and distinct variety.

1. Brilliant red-purple flowers, upper petals with weak scarlet 'eyes'
2. Semi double flower type, and medium to large, round inflorescences
3. Medium green foliage with relatively strong zonation
4. Medium to strong vigor, and well branched
5. Mounding habit (relatively high, but not very wide) with the flower heads well above the foliage 6. About mid season spring flowering response
7. Suitable as a bedding plant mainly, and for larger containers

COMPARISON WITH COMMERCIAL CULTIVARS

TABLE 1

DIFFERENCES BETWEEN THE NEW VARIETY 'AMRI PUR' AND SIMILAR VARIETIES

| | 'AMRI PUR' | 'FISRODEEP' (U.S. Ser. No. 12/228,729) |
|---|---|---|
| Flower color upper petals (RHS) | Between N66B and N74A (upper and lower petals), Upper petals with scarlet base | Between N66B and N74B, upper petals with white base; lower petals N74B |
| Leaf zone, distinctness (range from 1 absent to 9 very strong) | Strong (7) | Weak (3) |
| Inflorescences, diameter (in August 2008) | 9.5 cm | 9.5-10.5 cm |
| | 'AMRI PUR' | 'FISDELAV' (Co-Applied) |
| Flower markings | Upper petals with scarlet bases | Red 'eyes' on upper and lower petals |
| Main flower color | (Somewhat deeper) Between N66B and N74A | N74B |

Plant:

*Form, growth and habit.*—Medium to strong vigor, bushy, well branched and rounded habit, relatively high, but not very wide.

*Plant height.*—32 cm.

*Plant height* (*inflorescence included*).—Approximately 40 cm.

*Plant width.*—30–35 cm.

*Number of inflorescences per plant.*—About 15.

Stem:

*Number of branches.*—Approximately 20.

*Color of stem.*—Light green, RHS 143C, no anthocyanin.

*Length of stem.*—Approximately 15–25 cm.

*Diameter.*—0.8–1.0 cm.

*Length of internodes.*—2–3 cm.

*Texture.*—Covered with dense, very short hair.

Foliage:

*Immature, leaf color, upper surface.*—RHS 137C–137D.

*Lower surface.*—RHS 138A.

*Mature, leaf color, upper surface.*—RHS 137-B-137C.

*Lower surface.*—RHS 138A.

*Length.*—5.5–6.5 cm.

*Width.*—9.0–11.0 cm.

*Shape.*—Kidney-shape (reniform), with weak lobes, and with open base, somewhat wavy margins and palmate venation.

*Base shape.*—Cordate.

*Apex shape.*—Rounded.

*Margin.*—Bi-crenate.

*Texture.*—Velvety, both surfaces pubescent.

*Color of zone.*—Brown, RHS 166A, relatively strong.

*Width of zone.*—1.8–2.0 cm.

*Color of veins, upper surface.*—RHS 144A, indistinct.

*Color of veins, lower surface.*—RHS 145A.

*Petiole, color.*—RHS 143C.

*Petiole, length.*—Relatively long, approximately 8–12 cm.

*Diameter of petiole.*—3 mm.

*Texture.*—A little rough, densely covered with short hair (hirtellous).

Inflorescence:

*Start of flowering* (50% *of plants with open flowers*).—On May 4 (9 weeks old).

*Duration of flowering.*—Continuous flowering from late April throughout the summer.

*Lastingness of individual flowers.*—7–9 days.

*Number of inflorescences per plant.*—About 15.

*Type and shape of inflorescence.*—Umbel, nearly a complete sphere.

*Number of flowers and buds per inflorescence.*—About 40–50.

*Umbel diameter.*—9.5 cm on average.

*Umbel depth.*—Up to 9 cm.

*Color of peduncle.*—RHS 144A.

*Length of peduncle.*—About 16–20 cm.

*Peduncle diameter.*—3–4 mm.

*Texture.*—Both glandular hair and soft hair.

*Color of pedicel.*—Reddish-brown, of varying intensity, upper portion reddish-brown, RHS 178A or 181A, fading towards base.

*Length of pedicel.*—3.0–3.3 cm.

*Diameter of pedicel.*—1.5 mm.

*Texture.*—Short glandular hair.

Corolla:

*Form.*—Semi-double, cup shaped to wide open, not quite round, but with a gap between upper petals and lower petals.

*Flower diameter.*—4.8–5.1 cm.

*Depth of flower.*—Approximately 1.5 cm.

*Number of petals.*—7–9.

*Color upper petals, upper surface.*—Intermediate between RHS N66A and N74A, scarlet/orange-red bases, color near RHS 43A, but distinctness is weaker, size about ⅓ of the petal length.

*Color upper petals, lower surface.*—Near RHS 67B.

*Length of upper petals.*—2.6–2.8 cm.

*Width of upper petals.*—1.7–2.0 cm.

*Color lower petals, upper surface.*—Intermediate between RHS N66B and N74A.

*Color lower petals, lower surface.*—RHS 71D or slightly more reddish.

*Length of lower petals.*—2.5–2.6 cm.

*Width of lower petals.*—1.9–2.1 cm.

*Petal shape.*—Obovate.

*Apex shape.*—Rounded.

*Margin.*—Entire.

*Petal texture.*—Smooth, glabrous.

*Number of petaloids.*—1 or 2, narrower and smaller than petals.

*Color of petaloids.*—Between N66B and N74A, RHS 67B for the lower side.

*Length of petaloids.*—1.0 cm.

*Width of petaloids.*—0.3–0.8 cm.

Bud (just before opening):

*Color.*—Near 67A to 67B.

*Length.*—1.6–1.8 cm.

*Width.*—0.9–1.1 cm.
*Shape.*—Elliptical.

Calyx:
*Number of sepals.*—5.
*Color of sepals.*—Mainly green, RHS 143A to 143B, a little anthocyanin RHS 181A at base.
*Length of sepals.*—0.9–1.1 cm.
*Width of sepals.*—4 mm (largest sepal), 2–3 mm for the other ones.
*Sepal shape.*—Lanceolate.
*Apex shape.*—Acute.
*Margins.*—Entire.
*Texture.*—Glandular hairs, long soft hairs.

Reproductive organs:
*Pistil.*—1.
*Length.*—7–8 mm.
*Style color.*—RHS 53A, purple-red.
*Style length.*—3 mm.
*Stigma color.*—RHS 53B.
*Number of stamens.*—5–7.
*Length of anthers.*—2–3 mm.
*Anther color.*—RHS 47A.
*Length filaments.*—6–7 mm.
*Color of filaments.*—Nearly white, RHS 69D, at base; upper part pink, RHS 68A.
*Pollen amount.*—Moderate (usual amount for the species).
*Color of pollen.*—RHS 28A, yellow orange.
*Fertility/seed set.*—No seed set observed.

Disease/pest resistance: Has not been observed on this hybrid.

What is claimed is:

1. A new and distinct variety of *Pelargonium* plant named 'Amri Pur,' substantially as illustrated and described herein.

* * * * *

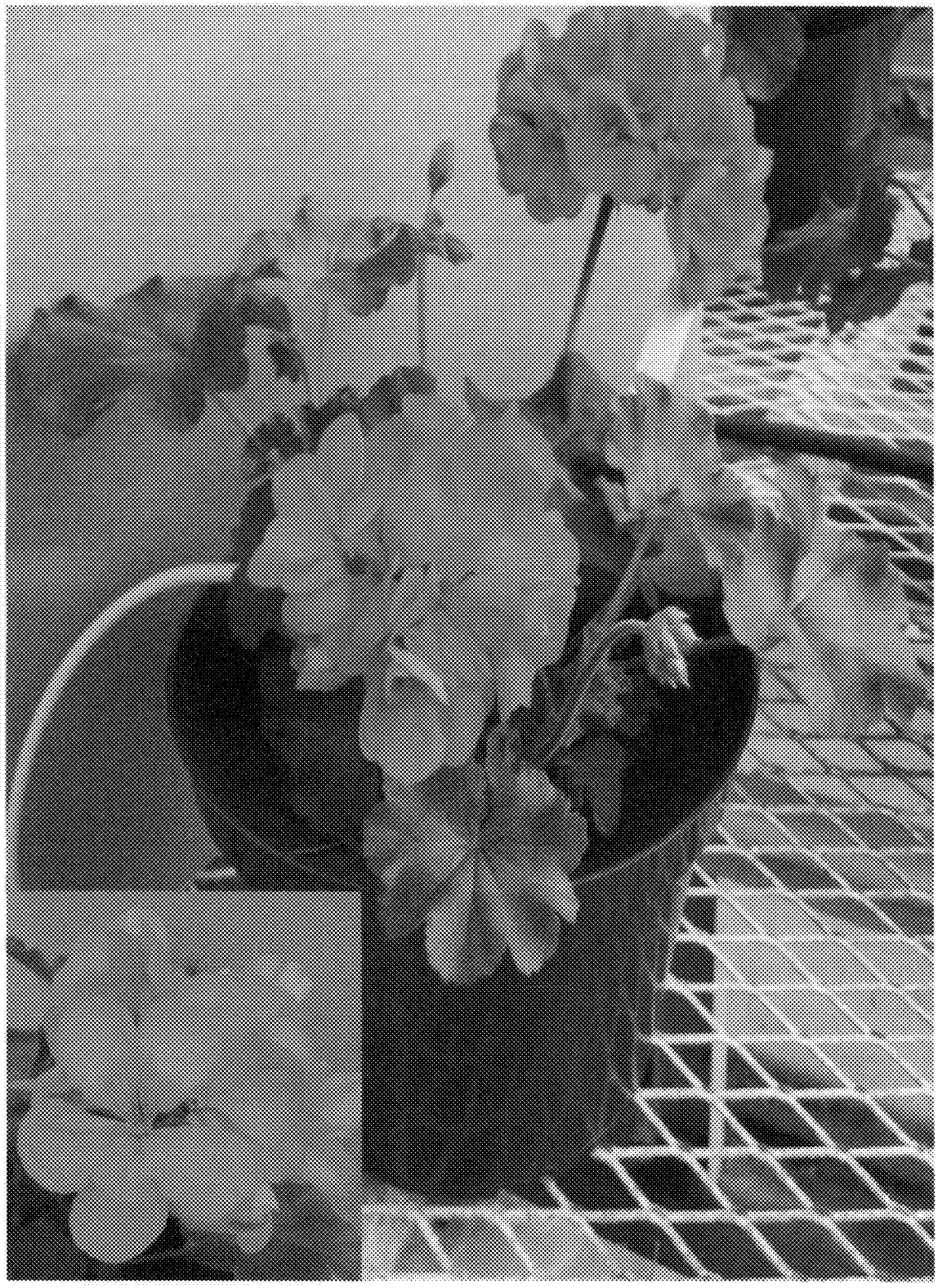

UNITED STATES PATENT AND TRADEMARK OFFICE

CERTIFICATE OF CORRECTION

PATENT NO. : PP 20,896 P2
APPLICATION NO. : 12/288822
DATED : March 30, 2010
INVENTOR(S) : Mitchell Hanes It is certified that error appears in the above-identified patent and that said Letters Patent is hereby corrected as shown below:

At column 3, line 54, delete "137-B-137C" and insert therefor --137B-137C--

Signed and Sealed this

Eleventh Day of May, 2010

David J. Kappos

David J. Kappos
*Director of the United States Patent and Trademark Office*